US011116865B2

United States Patent
Olson et al.

(10) Patent No.: US 11,116,865 B2
(45) Date of Patent: *Sep. 14, 2021

(54) ANTIMICROBIAL SILVER IODATE

(71) Applicant: Innovotech, Inc., Edmonton (CA)

(72) Inventors: Merle E. Olson, Calgary (CA); Patricia L. Nadworny, Sherwood Park (CA); Graeme Prosperi-Porta, Edmonton (CA)

(73) Assignee: Innovotech, Inc., Edmonton (CA)

( * ) Notice: Subject to any disclaimer, the term of this patent is extended or adjusted under 35 U.S.C. 154(b) by 77 days.

This patent is subject to a terminal disclaimer.

(21) Appl. No.: 16/548,062

(22) Filed: Aug. 22, 2019

(65) Prior Publication Data

US 2019/0374674 A1  Dec. 12, 2019

Related U.S. Application Data

(63) Continuation of application No. 14/415,666, filed as application No. PCT/CA2013/000658 on Jul. 19, 2013, now Pat. No. 10,434,210.

(60) Provisional application No. 61/673,385, filed on Jul. 19, 2012, provisional application No. 61/706,897, filed on Sep. 28, 2012.

(51) Int. Cl.
| | |
|---|---|
| *A61L 15/44* | (2006.01) |
| *A01N 59/12* | (2006.01) |
| *A01N 59/16* | (2006.01) |
| *A61K 33/38* | (2006.01) |
| *A61K 9/06* | (2006.01) |
| *A61K 9/00* | (2006.01) |
| *A61P 31/02* | (2006.01) |

(52) U.S. Cl.
CPC ............. *A61L 15/44* (2013.01); *A01N 59/12* (2013.01); *A01N 59/16* (2013.01); *A61K 9/06* (2013.01); *A61K 33/38* (2013.01); *A61K 9/0014* (2013.01); *A61L 2300/104* (2013.01); *A61L 2300/404* (2013.01)

(58) Field of Classification Search
CPC ............. A61L 15/44; A61L 2300/104; A61L 2300/404; A61K 9/06; A61K 33/38; A61K 9/0014; A01N 59/12; A01N 59/16
See application file for complete search history.

(56) References Cited

U.S. PATENT DOCUMENTS

| | | | |
|---|---|---|---|
| 4,060,676 A | 11/1977 | Dey et al. | |
| 5,614,568 A | 3/1997 | Mawatari et al. | |
| 6,231,848 B1 | 5/2001 | Breitenbach et al. | |
| 6,861,067 B2 | 3/2005 | McGhee et al. | |
| 9,723,843 B2 | 8/2017 | Olson et al. | |
| 10,434,210 B2 * | 10/2019 | Olson | ............ A61L 15/44 |
| 2005/0064176 A1 | 3/2005 | Terry | |
| 2007/0254044 A1 | 11/2007 | Karandikar et al. | |
| 2011/0244256 A1 * | 10/2011 | Song | ............ B05D 7/56 428/458 |
| 2011/0275518 A1 | 11/2011 | Marques et al. | |
| 2012/0058169 A1 | 3/2012 | Olson et al. | |

* cited by examiner

*Primary Examiner* — Mina Haghighatian
(74) *Attorney, Agent, or Firm* — Dinsmore & Shohl, LLP

(57) ABSTRACT

The present invention is silver (I) periodate compounds and their use in preventing or reducing microbial contamination. The invention includes gels, coatings, and articles of manufacture having a surface contacted or coated with a gel comprising an antimicrobial silver (I) compound. Methods of treatment are also disclosed.

20 Claims, No Drawings

ANTIMICROBIAL SILVER IODATE

CROSS-REFERENCE TO RELATED APPLICATIONS

The present application is a continuation of U.S. patent application Ser. No. 14/415,666, filed Jan. 19, 2015, which is a 371 International Patent Application of PCT/CA2013/000658, filed Jul. 19, 2013, which also claims priority from U.S. Provisional Application No. 61/706,897, filed Sep. 28, 2012, and U.S. Provisional Application No. 61/673,685, filed Jul. 19, 2012. The entire contents of each of these applications are hereby incorporated by reference herein.

FIELD OF THE INVENTION

This invention relates to silver iodate compounds, such as silver (I) periodates, and their use in treating, preventing, or reducing microbial contamination. These silver compounds are particularly suited to being formulated into gels or hydrogels without loss of their anti-microbial properties.

This invention also relates to antimicrobial compositions and the use of these compositions with various devices, preferably devices such as medical devices, in which having an antimicrobial property is beneficial.

The invention also relates to articles produced or formed using the antimicrobial compounds and compositions of the present invention.

The invention also relates to coatings and/or ingredients in the manufacture of devices where having an antimicrobial property is beneficial, e.g., a medical device, wound dressing, or an implant.

BACKGROUND OF THE INVENTION

Silver is known for its antimicrobial properties, particularly when incorporated into or onto medical devices. However, it is challenging to coat or incorporate silver onto a surface, whether medical devices or other surfaces (e.g., seeds, plants, metals, etc.). Many products formed using existing silver compounds are poorly soluble, exhibit poor silver release profiles, the silver is inactivated in body fluids, and the antimicrobial activity is designed for planktonic bacteria and shows little or no effect against biofilm. Further, many, if not all, higher oxidation state silver compounds (e.g., oxysilver nitrate and silver (III) periodates) cannot readily be mixed with commercial gel formulations; typically the silver compound does not mix well, or the silver compound reacts with the gel, resulting in loss of its antimicrobial activity and/or loss of gel properties.

One conventional approach for obtaining antimicrobial medical devices is the deposition of metallic silver directly onto the surface of the substrate (for example, by vapor coating, sputter coating, or ion beam coating). However, these noncontact deposition coating techniques suffer many drawbacks, including poor adhesion, lack of coating uniformity, and the need for special processing conditions, such as preparation in darkness due to the light sensitivity of some silver salts. One particular drawback of these coatings is that the processes by which the coatings are formed do not adequately coat hidden or enclosed areas, such as the interior lumen of a catheter or stent. Additionally, these methods produce coatings that act like metallic silver in that they do not release silver from the coating and require contact with the coating to provide any antimicrobial action. Because they do not release sufficient silver ions into aqueous fluids, they offer little or no protection from bacteria carried into the body upon application of the device and do not inhibit infection in the surrounding tissue or fluid.

Another method of coating silver onto a substrate involves deposition or electrodeposition of silver from solution. Drawbacks of previous deposition methods include poor adhesion, low silver pick-up on the substrate, complex manufacturing processes, the need for surface preparation, high labor costs, and the need for additional deposition agents and stabilizing agents.

Some silver coatings release, to varying degrees, silver ions into the solution or tissue surrounding the substrate. However, activation of such coatings often requires conditions that are not suitable for use with some medical implants. These conditions include abrasion of the coating surface, heating to a temperature above 180° C., contact with hydrogen peroxide, and treatment with an electric current.

Alternatively, a solid form of the silver salt can be mixed with a finely divided or liquefied polymeric resin, which is then molded into the article. Further, the antimicrobial compound can be mixed with monomers of the material prior to polymerization.

There are several disadvantages to this last approach: larger quantities of the antimicrobial material are required to provide effective antimicrobial activity; it is also difficult to produce articles that actually release the antimicrobial ions because most coatings absorb little, if any, water to aid in the diffusion and release of the antimicrobial ions, resulting in articles that provide only a limited antimicrobial effect.

There is also a need for compositions that overcome the solubility, settling, and agglomeration problems of conventional antimicrobial compositions, and exhibit enhanced, sustained release of antimicrobial agents. There is also a need for antimicrobial compositions that may be incorporated into a gel or hydrogel used to make or coat a device, while retaining its antimicrobial effectiveness. There is also a need for antimicrobial compositions that are stable, e.g., thermally stable, light stable, stable in the materials they are included on/with, and are not inactivated in the environment of their intended use.

SUMMARY OF THE INVENTION

The compositions and methods of the present invention comprise one or more silver iodate compounds and their use as antimicrobial agents. The invention also includes articles of manufacture that include one or more of these compounds as a layer or coating on the article.

The compositions and methods of the present invention have applicability in a wide variety of agricultural, industrial, and medical environments, e.g., disinfecting any surface, particularly disinfecting work or processing surfaces (e.g., tables); in antimicrobial coatings; in medical devices and implants, particularly where having an antimicrobial property or characteristic would be beneficial; and in treating human, plant, and animal diseases and conditions.

The compositions and methods of the present invention are also effective in preventing, treating, and/or eradicating biofilm.

Some of the active agents of the present invention have a small grain size, exhibit polycrystallinity, and have a surface area that, in combination, result in greater antimicrobial activity.

DETAILED DESCRIPTION OF THE INVENTION

The present invention involves silver iodate compounds, such as silver (I) periodates, and their use as antimicrobial agents. Some embodiments of the invention include one or more silver iodate compounds as an active agent(s) imparting an antimicrobial property or properties. The present invention also involves the use of one or more of these active agents to impart an antimicrobial property or properties to a gel or a hydrogel.

In accordance with the present invention, the active agent includes a family of silver (I) periodate compounds. All of the members of the family are silver (I) combined with a higher oxidation state iodine and an oxidized silver ion, e.g. $Ag_5IO_6$ or $Ag_2H_3IO_6$. The inventors believe that the iodine structure facilitates silver transfer, in a form such as $[Ag_2IO_6]^{3-}$, through the biofilm structure or matrix. The inventors also believe that the silver ions, which are present in both the cation ($[Ag_3]^{3+}$) and the anion ($[Ag_2IO_6]^{3-}$), combined with the iodate ions, provide multiple antimicrobial methods of action, thus providing improved antimicrobial activity as compared to conventional compounds.

Compounds of the present invention include, but are not limited to, silver (I) iodate; pentasilver hexaoxoiodate; $Ag_5IO_6$; silver orthoperiodate; silver periodate (VII); silver iodate (VII); $5Ag_2OI_2O_7$; $Ag_2H_3IO_6$; $Ag_xH_yIO_6$, where x+y=5; $Ag_xM_yIO_6$, where the total cationic charge of x+y=5 and M is one or more cations; and combinations thereof. In preferred embodiments of the invention, the cation, M, may be selected from the group consisting of K, Na, Mg, Ca, Au, Pt, Cu, and Fe. The most preferred cations are potassium and sodium.

The compounds of the present invention may be used by themselves, may be an ingredient in a composition, or may be a part or element of an article of manufacture (e.g., a wound dressing, a gel, a medical grade metal, or a catheter). The compounds of the present invention may be combined with and/or formulated into a composition. In preferred embodiments of the invention, one or more active agents (e.g. a silver (I) periodate) are an ingredient in a gel or a gel formulation.

Any of the active agents of the present invention may be used to impart antimicrobial properties wherever it is needed, e.g., topically, or to a surface or a substrate. For example, one or more active agents may be incorporated into the structure of substrate or as a coating or the like. Exemplary substrates include metals, wound dressings, medical devices and instruments; and plants, including seeds and leaves. The surface may be internal or external; or the device may be used internally. The active agent(s) and/or formulations of the present invention may be directly applied to a surface, e.g., directly to a human, animal, or plant infection or wound (e.g., applied topically to a wound).

The silver (I) periodate family of compounds of the present invention may be produced or synthesized by following processes already known to those skilled in the art. Examples of these processes include:

(1) Kovalevskiy, A., and Jansen, M. Synthesis, Crystal Structure Determination, and Physical Properties of $Ag_5IO_6$. Z Anorg Allg Chem 2006; 632:577-581.

(2) Cignini, P., Icovi, M., Panero, S., and Pistoia, G. On the possibility of using silver salts other than $Ag_2CrO_4$ in organic lithium cells. J Power Source 1978; 3:347-357.

(3) Chapter 9. Oxysalts of Iodine. In: High Temperature Properties and Thermal Decomposition of Inorganic Salts. 2001, CRC Press LLC.

(4) Mackay, Mackay, and Henderson. Introduction to modern inorganic chemistry, pg. 489.

(5) Gyani, P. Periodic Acid and Periodates. II The system silver oxide-periodic acid-water at 35° C. J Phys Chem 1951; 55(7):1111-1119.

(6) International Patent Application No. PCT/CA2011/000941, filed 22 Aug. 2011, incorporated herein by reference in its entirety.

The present invention also includes methods of coating a surface or a substrate with an active agent of the present invention, said methods resulting in imparting an antimicrobial characteristic to the substrate. The present invention also includes methods of coating a wound dressing substrate with a gel comprising an active agent of the present invention, said methods resulting in imparting an antimicrobial characteristic to the substrate. As used herein, wound dressing substrate includes but is not limited to a wide variety of wound dressing substrates, including polymer-based substrates such as high density polyethylene and polyester, and organic based substrates such as cotton and rayon, and gels.

The compositions and methods may also include one or more other active agents.

In some embodiments of the invention, one or more silver (I) periodate compounds are used to produce an article having improved antimicrobial characteristics. In some of these embodiments of the invention, the silver (I) periodate compound may be in a coating, gel, hydrogel, or the like on a surface of the article, or may be incorporated into a material that forms the article. In some embodiments of the invention, the article comprises titanium or stainless steel. In some embodiments of the invention, the article is a medical device, such as a catheter, endoscope, wound dressing, or needle. Some embodiments of the invention include forming an article including an active agent of the present invention, thereby forming an article having one or more antimicrobial properties.

For one or more the active agents of the present invention, the small grain size (with a larger particle size) contribute to enhanced or improved antimicrobial activity. For example, $Ag_5IO_6$ has a grain size of about 15 Å (fifteen angstroms), that is, a nano size, and a particle size that is much larger (typically between about 2 and 20 μm, that is, not nano). The grain size may increase with some forms of processing or post-synthesis processing, e.g., heating, exposure to solutions or solvents, grains growing together, grains combining into a single larger grain, and the like.

Some embodiments of the invention include a coating, layer, or the like on an article, said coating, etc., comprising one or more active agents of the present invention, and imparting improved antimicrobial characteristics to the article or a portion of the article.

In some embodiments of the invention, the composition may be any form that does not inactivate the silver, including but not limited to a gel, ointment, cream, foam, or ingredient or layer in a polymer, substrate, or carrier.

In some embodiments of the invention, the active agent or a composition containing the active agent may be any form that does not inactivate the silver, including but not limited to a layer; or ingredient in a metal, polymer, or organic material; or a carrier. The preferred forms are a silver (I) periodate powder, or a coating that includes a silver (I) periodate.

In some embodiments of the invention, the compositions and methods are used for treating a microbial contaminant using an antimicrobial agent comprising silver ions or silver-containing complexes. The compositions and methods may also include one or more other active agents. The compositions and methods are antimicrobial, e.g. against biofilm, similar structures, or precursors formed by bacteria, fungi, viruses, algae, parasites, yeast, and other microbes. A microbial contaminant or infection may be found in a variety of species, including but not limited to humans, pigs, ruminants, horses, dogs, cats, plants, and poultry.

In some embodiments of the invention, the active agent(s) may be incorporated into or onto packaging for an article, such as a medical device or a needle.

In some embodiments of the invention, one or more active agents or one or more starting materials may be used for the manufacture of a medicament intended to treat or prevent infections or contamination, particularly infections caused by bacteria, bacteria-like organisms, fungi, yeast, or biofilms.

The silver compositions of the present invention may be used to coat, or may be incorporated into, any article comprising a metal or metal alloy. Typical metals and alloys include, but are not limited to titanium, titanium containing alloys, aluminum, stainless steel, mild steel, and copper. In preferred embodiments of the invention, the metal is titanium (grade 2), titanium (grade 5), aluminum, stainless steel, stainless steel needles, titanium (grade 5) pins, and other titanium (grade 5) implants.

In some embodiments, the compositions optionally contain other components that provide beneficial properties to the composition, that improve the antimicrobial effectiveness of the composition, or that otherwise serve as active agents to impart additional properties to the composition. The compositions are also used to inhibit algal, fungal, mollusk, or microbial growth on surfaces. The compositions of the invention are also used as herbicides, insecticides, antifogging agent, diagnostic agents, screening agents, and antifoulants.

In another embodiment, the composition may be applied as a coating to a preformed article, part of an article, a plant or portion thereof (e.g., a seed or a leaf), or a substrate. The coating may be produced, for example, by dipping the article, etc., into the composition or by spraying the article with the composition and then drying the coated article.

Some embodiments of the present invention include providing compositions that provide antimicrobial, antibacterial, antiviral, antifungal, anti-biofilm, or antibiotic activity, or some combination thereof.

Some embodiments of the present invention include providing compositions that reduce encrustation, inhibit coagulation, improve healing, inhibit restenosis, or impart antiviral, antifungal, antithrombogenic, or other properties to coated substrates.

As described in more detail below, the methods and compositions of the present invention may be used wherever microorganisms, biofilm or similar structures may be found, including but not limited to microorganisms growing and/or floating in liquid environments. The antimicrobial or anti-biofilm effect may be biostatic or biocidal.

In some embodiments of the invention, the compositions and methods may be used to treat or prevent one or more biofilms. In some embodiments of the invention, the compositions and methods may be used to treat and/or prevent one or more human, animal, or plant diseases, conditions, infections, or contaminations. Typically these diseases and infections, etc., are caused by microbes associated with or residing in the biofilm.

The present invention includes any method of contacting with an antimicrobial agent of the present invention. Typical mechanisms of contacting include, but are not limited to, coating, spraying, immersing, wiping, and diffusing in liquid, powder, or other delivery forms (e.g., injection, tablets, by syringe (e.g., topical or internal), washing, vacuum, or oral). In some embodiments of the invention, the compositions and methods may include applying the active agent to any portion of an article or an ingredient of an article.

The Examples provide experimental confirmation that the silver (I) periodate compounds of the present invention release silver over time. These Examples therefore demonstrate that stable, slow release silver-containing compounds can be used as long-lasting antimicrobials against bacterial and fungal pathogens, including biofilms growing on a substrate or layer.

These compositions exhibit antimicrobial activity and/or anti-biofilm activity against a variety of microbes, including both bacteria and fungi, and provide a sustained release of silver ions or silver containing complexes from silver compounds.

In preferred embodiments of the invention, antimicrobial properties may be achieved by contacting an antimicrobially active silver species within or at the surface of a substrate, or diffusing from the surface of a substrate into an aqueous environment.

The silver compounds may be used in any of the following formats: silver deposition coatings, liquid, suspension, powder, capsule, tablet, coating, incorporation, and similar configurations. In a preferred embodiment of the present invention, active agents are incorporated directly onto or into a material, or may be incorporated by sequentially adding components or precursors of the active agent to the material, and having the precursors of the active agent in or on the coating. Other forms also include films, sheets, fibers, sprays, and gels.

Examples of additional antimicrobial agents which may be included along with the actives described above are known to those skilled in the art and include, but are not limited to: streptomycin, tetracycline, erythromycin, ciprofloxacin, doxycycline, ampicillin, penicillin, gentamicin, and heavy metals including, but not limited to, gold, platinum, silver, zinc, and copper, and their combined forms including salts, such as chloride, bromide, iodide, nitrate, sulphate, and periodate, complexes with carriers, and other forms.

Multiple inactive ingredients may be optionally incorporated in the formulations. Examples of such ingredients are emulsifiers, thickening agents, solvents, anti-foaming agents, preservatives, fragrances, coloring agents, emollients, fillers, and the like.

In this aspect of the invention, the compositions and methods are suitable for treating against one or more microbial infections, including but not limited to diseases or conditions caused by *Pseudomonas aeruginosa, Staphylococcus aureus, Klebsiella pneumoniae, Clostridium difficile, Candida albicans, Staphylococcus epidermidis, Escherichia coli, Streptococcus* spp, *Pseudomonads, Xanthomonads*, and *Curtobacterium* species.

The active agents of the present invention may also be used to treat plant pathogens, including but not limited to *Pseudomonas syringae* pv. *syringae, Pseudomonas syringae* pv. *phaseolicola*, and *Curtobacterium flaccumfaciens* pv. *flaccumfaciens*.

The compositions may be used to coat substrate materials. Thus, another aspect of the invention is a coating containing the composition of the invention. These coatings may comprise either a single layer or multiple layers. The compositions of the present invention are used alone or in combination with polymer coatings to provide advantageous properties to the surface of the substrate.

The compounds of the present invention and/or their reaction products may be incorporated into any wound dressing, bandage, or wound healing product.

The active agents of the present invention may also be formulated into a composition comprising a solvent with short term stability. Exemplary solvents include, but are not limited to, water, saline (where some initial breakdown occurs but appears to be self-limited), methanol, acetone, acetonitrile, and tetrahydrofuran.

Definitions

The following definitions are used in reference to the invention:

As used herein, active agent describes a silver-containing chemical substance, compound, or complex that exhibits antimicrobial activity, and is Ag (I) combined with a higher oxidation state iodine and coordinated with oxygen atoms. Active agent includes but is not limited to a silver (I) periodate; one or more reaction products of a sodium diperiodatoargentate, each of these reaction products containing iodine; one or more reaction products of a potassium diperiodatoargentate, each of these reaction products containing iodine; pentasilver hexaoxoiodate; $Ag_5IO_6$; silver orthoperiodate; silver periodate (VII); silver iodate (VII); $5Ag_2OI_2O_7$; $Ag_2H_3IO_6$; and other combinations of $Ag_xH_yIO_6$ where x+y=5; $Ag_xM_yIO_6$, where the total cationic charge of x+y=5 and M is one or more cations; and combinations thereof. One skilled in the art will readily recognize that the cation can be any of a large number of cations. Exemplary cations include but are not limited to K, Na, Mg, Ca, Au, Pt, Cu, and Fe. The preferred cations are K and Na. Active agent also includes compositions comprising one or more active agents.

Reaction product, as used herein, refers to any silver containing compound or complex in the silver iodate family, formed by any number of different reaction processes. Exemplary reaction products include but are not limited to pentasilver hexaoxoiodate; $Ag_5IO_6$; silver orthoperiodate; silver periodate (VII); silver iodate (VII); $5Ag_2OI_2O_7$; $Ag_2H_3IO_6$; and other combinations of $Ag_xH_yIO_6$ where x+y=5, $Ag_xM_yIO_6$, where the total cationic charge of x+y=5 and M is one or more cations (including those specified above); and combinations thereof. All of the starting materials form at least one compound or complex that releases silver.

As used herein, antimicrobial includes antibacterial, including planktonic or biofilm forms. A preferred antimicrobial compound or composition is also anti-biofilm. Anti-biofilm agent refers to any element, chemical, biochemical, or the like that is effective against a biofilm. Typical anti-biofilm agents are those that have antimicrobial, antibacterial, anti-fungal or anti-algal properties. Metal and metal compounds, preferably ionic silver-containing species, have been shown generally to have antibacterial and ethylene inhibiting properties, and are preferred anti-biofilm agents in accordance with the present invention. In some embodiments of the invention, the anti-biofilm agent is a broad spectrum agent, e.g., having effectiveness or activity against more than one microbial species.

"Sustained release" or "sustainable basis" are used to define release of atoms, molecules, ions, or clusters of a noble metal that continues over time measured in hours or days, and thus distinguishes release of such metal species from the bulk metal, which release such species at a rate and concentration which is too low to be effective, and from highly soluble salts of noble metals such as silver nitrate, which releases silver ions virtually instantly, but not continuously, in contact with an alcohol, aqueous solution, or electrolyte. The active agents of the present invention are superior to other commercially available silver containing compounds in part because of the slow release of silver.

Medical device as used herein refers to any device, tool, instrument, implant, or the like, relating to medicine or the practice of human or veterinary medicine, or intended for use to heal or treat a disease or condition. A medical device of the present invention may be used for the medical benefit of a human or animal, including laboratory or hospital equipment. A medical device or a component of a medical device may include all natural and synthetic materials and both fibrous and non-fibrous materials. For example, the materials may be comprised of a metal, plastic, paper, glass, ceramic, textile, rubber, polymer, composite material or any other material or combination of materials. Exemplary medical devices include, but are not limited to, catheters; cannulae; needles; stents; guide wires; implant devices; filters; endoscopes; surgical or medical instruments; stents of any size, shape, or placement; coils of any size, shape, or placement; contact lenses; IUDs; peristaltic pump chambers; endotracheal tubes; gastroenteric feeding tubes; arteriovenous shunts; condoms; oxygenator and kidney membranes; gloves; pacemaker leads; wound dressings; metallic pins, plates, and screws; metallic artificial hips; artificial knees; and gels, creams, and ointments.

Surface, as used herein generally refers to its common dictionary definition, e.g., an outer face, outside, or external boundary of a thing or a portion of a thing. The surface will generally be an external portion, but in some embodiments, the surface may be internal. A surface may also include an outer portion of a device or thing, but the outer portion need not be the farthest outer portion or layer. For example, some medical devices such as catheters are known to include one or more coatings or layers. Any or all of these individual coatings or layers are still considered to be on the surface of the device. Similarly, when applied to a human, animal, or plant, a surface may be the skin or the like, including but not limited to an infection or wound on that surface.

Surface contamination, as used herein, refers to microorganisms growing on or relocated to a surface. The microorganisms associated with surface contamination may be actively growing or dormant, but represent a viable inoculum that can reinitiate infection, disease, or other undesirable conditions.

Antimicrobial activity is art-recognized and may be biostatic and/or biocidal. Biostatic materials are materials that inhibit the growth of all or some of the microorganism; and a biocide is a material that kills all or some of the microorganism. The active agents of the present invention are sufficiently soluble to provide biostatic and/or biocidal activity.

The term "coating" as used herein generally includes coatings that completely cover a surface, or a portion thereof, as well as coatings that may only partially cover a surface, such as those coatings that after drying leave gaps in coverage on a surface. The latter category of coatings may include, but are not limited to a network of covered and uncovered portions (e.g., non-continuous covered regions of the surface). When the coatings described herein are described as being applied to a surface, it is understood that the coatings need not be applied to, or that they need not cover, the entire surface. For instance, the coatings will be considered as being applied to a surface even if they are only applied to modify a portion of the surface. The coating may be applied to a surface or impregnated within the material used to construct an item or a portion of an item. The preferred coating is a gel or hydrogel (e.g., U.S. Pat. No. 5,662,924).

The term "substrate" as used herein generally refers to a body or base layer or material (e.g., onto which other layers are deposited). A substrate may be organic (e.g., cotton or wool), metal, a polymer (e.g., rayon or polyester), or cellular (e.g., a plant, a seed, leaves, skin, or hide). Metal substrate includes but is not limited to a wide variety of metals (e.g., titanium and stainless steel); metal alloys; and devices or products made using these metals (e.g., medical devices, needles, ports, implants, pins, etc.). In accordance with the present invention, the substrate must not inactivate the silver compound, or inactivate it to the extent that the silver is no longer suitable for use as an anti-microbial agent.

EXAMPLES

Example 1—Basic Compatibility of $Ag_5IO_6$ with Gels

The purpose of this study was to determine whether $Ag_5IO_6$ could be incorporated into various gels without reacting with the gels. $Ag_5IO_6$ powder was combined with various commercially available hydrogels and then visually examined for stability, along with UV-Vis analysis and x-ray diffraction.

Gels selected: Guardian Laboratories AquaThik™ (Xanthan gum, PEG-180; 3% in water); Lubrajel® RC (Water, glycerin, propylene glycol, polyacrylic acid, sodium polyacrylate, 0.18% methylparaben, 0.02% propylparaben), and Lubrajel® PF (Glycerin, glyceryl acrylate/acrylic acid copolymer); SteriLub™ (unknown composition); BASF Pluronic® F127+Carbowax 600 (Polyoxyethylene-polyoxypropylene block copolymer; 18% Pluronic, 15% Carbowax 600); ConvaTec DuoDerm® Hydroactive® Sterile Gel (pectin, sodium carboxymethylcellulose); Molnlycke Normlgel® (0.9% NaCl, $H_2O$, xanthan gum); Smith&Nephew IntraSite Gel (Water >60%, propylene glycol 10-30%, absorbent polymer <10%—crilanomer, a Graft-T starch copolymer) and SoloSite Gel (Water >60%, glycerol 10-30%, absorbent polymer <10%, allantoin <1%, antiseptic/preservative <1%); carboxymethylcellulose gel (4% in water); Cremophor; and Gelrite (0.4% in water).

For each gel, the samples were mixed in a small glass container with fine $Ag_5IO_6$ powder to generate 500 ppm $Ag_5IO_6$ in the gels. Each of the above formulations were examined for visual signs of instability, such as dramatic viscosity changes, color changes, release of gas, deposition of precipitate that appears different from the original $Ag_5IO_6$, and temperature change during stirring (heat release).

UV-Vis Analysis: Samples were diluted to 1/10th their original concentration. For UV-Vis blanks, control gels (with no $Ag_5IO_6$) were prepared as described for each gel, and diluted to 1/10$^{th}$ as well. UV-Vis measurements were performed between 190-500 nm.

pHs of the gel formulations were measured with and without the $Ag_5IO_6$ added using pH indicator strips.

No viscosity change, gas release, temperature change, or pH change occurred after the addition of $Ag_5IO_6$ to the AquaThik™. A color change from clear to translucent purple occurred, but no UV-Vis peaks were observed. XRD results showed that the $Ag_5IO_6$ remained 100% pure and thus did not react with the AquaThik™ gel to form a new crystalline compound.

No viscosity change, color change, temperature change, UV-Vis peaks, or pH change was detected after the addition of the $Ag_5IO_6$ to the SteriLub™ gel. The $Ag_5IO_6$ did not evenly disperse or dissolve; instead it formed small clusters of particles. During mixing, large gas bubbles formed, which were not due a reaction but rather incorporation of air. The XRD results showed that the $Ag_5IO_6$ did not react with the gel to form a new crystalline compound (remained 100% pure after mixing).

The Pluronic® F127 plus Carbowax 600 went through a change in viscosity, color, and a large amount of finely distributed gas bubbles formed in the gel. The initially clear Pluronic® F127 turned white and developed a porous consistency. $Ag_5IO_6$ was not visible in the Pluronic® F127 after addition. No temperature change, precipitate formation, or pH change occurred after the addition of the $Ag_5IO_6$. A peak at 216 nm was measured by UV-Vis, likely due to dissolved $Ag_5IO_6$. A sample was not submitted for XRD because of the undesirable physical changes in the gel after addition of $Ag_5IO_6$.

The DuoDerm® did not undergo any change in viscosity, pH or temperature from the addition of $Ag_5IO_6$. The gel color changed to a darker brown, and very small quantities of $Ag_5IO_6$ were still noticeable in clumps. A peak at 216 nm was measured by UV-Vis, likely due to dissolved $Ag_5IO_6$. The XRD data obtained shows that the $Ag_5IO_6$ did not react with the DuoDerm® hydrogel to form a new crystalline compound but remained pure.

There was no viscosity change, temperature change, pH change or release of gas from the carboxymethylcellulose after the addition of $Ag_5IO_6$. The carboxymethylcellulose turned from clear to a dark brown color. The $Ag_5IO_6$ was not visible as clumps, and no new precipitates were observed to have formed. A UV-Vis peak was measured at 214 nm, likely due to dissolved $Ag_5IO_6$. The XRD data showed that the carboxymethylcellulose was not reactive with the $Ag_5IO_6$.

There was no viscosity change, temperature change, pH change, release of gas, or obvious precipitation formation in the Normlgel® after the addition of the $Ag_5IO_6$. The Normlgel® changed to a translucent brown and no clumps of $Ag_5IO_6$ were visible in the gel. A UV-Vis peak was measured at 216 nm, likely due to dissolved $Ag_5IO_6$ or AgCl. The XRD data shows that the Normlgel® contained KCl and AgCl, as well as $Ag_5IO_6$. The Normlgel® blank contained NaCl and KCl. Thus the AgCl was likely formed by the breakdown of $Ag_5IO_6$ with release of $Ag^+$ which then reacted with the NaCl contained in the gel, suggesting that $Ag_5IO_6$ is incompatible under these conditions with this gel for long term storage.

The Lubrajel® PF did not have any change in viscosity, temperature, pH or color after the addition of $Ag_5IO_6$. No precipitate formed and no gas was released. The $Ag_5IO_6$ agglomerated, forming larger particles than originally added to the gel. A UV-Vis peak was measured at 214 nm, likely due to dissolved $Ag_5IO_6$. The XRD data showed that only $Ag_5IO_6$ was present in the gel, indicating that the $Ag_5IO_6$ had not reacted with the Lubrajel® PF hydrogel.

The Lubrajel® RC did not undergo any change in viscosity, temperature, pH or color after the addition of $Ag_5IO_6$. Also, no precipitate formed and no gas was released. The $Ag_5IO_6$ agglomerated, forming larger particles than what was originally added to the gel. The UV-Vis data showed peaks or spikes at 230 nm and 284 nm of uncertain identity. The XRD data showed that the Lubrajel® RC only contained $Ag_5IO_6$, indicating the $Ag_5IO_6$ did not react in Lubrajel® RC.

There was no change in the viscosity, pH, or temperature of the IntraSite gel and no gas was released after $Ag_5IO_6$ addition. The color of the IntraSite* became translucent brown and no $Ag_5IO_6$ particles were visible in the gel. A UV-Vis peak was detected at 210 nm, suggesting dissolved $Ag_5IO_6$. The XRD data showed that only $Ag_5IO_6$ was present in the gel—no reaction products.

There was no change in the viscosity, pH, or temperature in the SoloSite gel and no gas was released after the addition of $Ag_5IO_6$. The color of the SoloSite became translucent brown and no $Ag_5IO_6$ particles were visible in the gel. UV-Vis data showed a peak at 286 nm, the origin of which was uncertain. The XRD data showed that only $Ag_5IO_6$ was present in the gel—no reaction products.

There was no change in viscosity, temperature, pH, UV-Vis signal, or color of the Cremophor gel after the addition of $Ag_5IO_6$, nor was there gas release. The $Ag_5IO_6$ dispersed within the gel, but particles were still visible. There was no $Ag_5IO_6$ detected by the XRD analysis. This could be due to a high level of interference from the Cremophor which hid the $Ag_5IO_6$ signal or a reaction of $Ag_5IO_6$ with the Cremophor gel. Since no other species of silver were detected, the latter cannot be confirmed.

The Gelrite did not undergo a change in viscosity, pH, or temperature after the addition of $Ag_5IO_6$, or release gas. The $Ag_5IO_6$ initially formed clumps, but after approximately ten minutes there was no sign of solid $Ag_5IO_6$ in the gel. The color became translucent brown as the $Ag_5IO_6$ dissolved in the gel. The XRD data showed that the $Ag_5IO_6$ did not react with the Gelrite.

The SoloSite, IntraSite, carboxymethylcellulose, Duo-Derm®, and AquaThik™ appear to incorporate $Ag_5IO_6$ well.

The Lubrajel® RC and PF, as well as the Sterilub™, are also but better dissolution/dispersion of the $Ag_5IO_6$ within the gel would be valuable.

Example 2—Antimicrobial Activity of $Ag_5IO_6$-Containing Gels

The purpose of this study was to measure anti-microbial activity using a relevant microorganism against $Ag_5IO_6$ incorporated into two representative hydrogels. This test method describes the physical combination of $Ag_5IO_6$ powder into two representative commercially available hydrogels and application of these hydrogels into a dressing material. These coated dressings were then tested in a day-to-day transfer corrected zones of inhibition assay. Each sample set was tested against *P. aeruginosa* (ATCC 27853). Samples were prepared as described in Example 1.

| | |
|---|---|
| AT-500 | Guardian Lab. AquaThik ™ 500 ppm |
| AT-1000 | Guardian Lab. AquaThik ™ 1000 ppm |
| AT-5000 | Guardian Lab. AquaThik ™ 5000 ppm |
| AT-10000 | Guardian Lab. AquaThik ™ 10000 ppm |
| RC-500 | Guardian Lab. Lubrajel ® RC 500 ppm |
| RC-1000 | Guardian Lab. Lubrajel ® RC 1000 ppm |
| RC-5000 | Guardian Lab. Lubrajel ® RC 5000 ppm |
| RC-10000 | Guardian Lab. Lubrajel ® RC 10000 ppm |

Rayon/polyester blend dressings were aseptically cut into 1 inch by 1 inch squares. In triplicate, the gels at different concentrations were spread on one side of the dressing to saturate it with gel. The weight of the gel added was determined. From a fresh streak plate, the study organism was inoculated in broth and incubated overnight, then used full strength. 300 μL of inoculum was pipetted onto three separate locations of large Petri plates and spread. Dressings were aseptically placed onto the plates. Plates were incubated overnight. The zones of inhibition were determined by measuring the diameter of the clear zone and the diameter of the test article with calipers in two perpendicular directions. The diameter of the test article was then subtracted from the diameter of the clear zone to yield the corrected zone of inhibition (CZOI). The above steps were repeated, transferring the samples to fresh lawns of bacteria each day until either no zone was produced or 9 transfers had been performed.

| | Amount of $Ag_5IO_6$ added to bandages | | |
|---|---|---|---|
| Sample | Gel Weight (g) | $Ag_5IO_6$ on bandage (mg) | Average $Ag_5IO_6$/ bandage area (mg/cm²) |
| AT - 500 | 0.25 | 0.13 | 0.02 |
| | 0.26 | 0.13 | |
| | 0.27 | 0.14 | |
| AT - 1000 | 0.25 | 0.25 | 0.04 |
| | 0.28 | 0.28 | |
| | 0.31 | 0.31 | |
| AT -5000 | 0.29 | 1.45 | 0.22 |
| | 0.31 | 1.55 | |
| | 0.30 | 1.50 | |
| AT - 10000 | 0.31 | 3.10 | 0.45 |
| | 0.31 | 3.10 | |
| | 0.34 | 3.40 | |
| RC - 500 | 0.37 | 0.19 | 0.02 |
| | 0.35 | 0.18 | |
| | 0.33 | 0 17 | |
| RC - 1000 | 0.28 | 0.28 | 0.04 |
| | 0.31 | 0.31 | |
| | 0.30 | 0.30 | |
| RC - 5000 | 0.26 | 1.30 | 0.2 |
| | 0.29 | 1.45 | |
| | 0.32 | 1.60 | |
| RC - 10000 | 0.33 | 3.30 | 0.46 |
| | 0.33 | 3.30 | |
| | 0.32 | 3.20 | |

The 500 ppm Aquathik gel had zones of inhibition for 1 day, the 5000 ppm Aquathik gel had zones of inhibition for 4 days, and the 10000 ppm Aquathik gel had zones of inhibition for 6 days. The 500 ppm Lubrajel RC had zones of inhibition for 1 day, the 5000 ppm Lubrajel RC had zones of inhibition for 4 days, and the 10000 ppm Lubrajel RC had zones of inhibition for 4 days. The 10000 ppm Aquathik gel performed the best out of all the gels. It had zones of inhibition that lasted the longest as well as having significantly larger zones than the 10000 ppm Lubrajel RC gel on Days 2, 3, and 4.

Example 3—$Ag_5IO_6$ Solubility in Water and Saline

The purpose of this study was to develop a basic understanding of the solubility (and stability) of $Ag_5IO_6$ in pure water and 0.9% (physiological saline), following OECD Method (105)—flask.

The solubility of $Ag_5IO_6$ is much lower in saline (0.61±0.05 mg/L) than in $ddH_2O$ (24.41±0.87 mg/L). This is likely due to a combination of reaction with the $Cl^-$ and overall ionic strength in the solution reducing the amount of $Ag_5IO_6$ dissolvable. The pH in saline (10) was consistently higher than the pH in $ddH_2O$ (8). The solids in the presence of saline were a lighter brown than the solids in $ddH_2O$.

While the UV-Vis spectra for the solutions in $ddH_2O$ and saline had one peak in common at about 206-212 nm, there was a shoulder at about 196-200 nm that was only present in the $ddH_2O$ sample, possibly indicating some reaction of the $Ag_5IO_6$ with the saline. However the spectrum for $Ag_5IO_6$ in saline did not match that for AgCl.

The XRD data indicated that in saline, approximately 25% of the solid material collected at the end of the experiment was converted to AgCl, with the remainder as unreacted $Ag_5IO_6$. In $ddH_2O$, approximately 99.9% of the solid material remained as $Ag_5IO_6$ with 0.1% being converted to Ag metal.

Example 4—$Ag_5IO_6$ Stability in Solvents

The purpose of this study was to determine whether or not $Ag_5IO_6$ interacts with methanol, tetrahydrofuran, acetone, and acetonitrile. 2-3 mm of $Ag_5IO_6$ was placed in a vial, 2 mL of the solvent was added, and the vial was placed in a TAM III for an isothermal run at room temperature for >24 h with solvent only as the reference. The heat flow was measured. After the run was complete, the solvents were allowed to flash off and the solids collected were submitted to XRD. Samples exposed following essentially the same method for only 18 h were also submitted for XRD $Ag_5IO_6$ can be blended with all solvents for <18 h without substantial reaction at room temperature. Acetone is the first to show significant reaction (onset about 14 h-18 h), followed by methanol (onset about 33 h), then THF (onset about 56 h), then acetonitrile (slower onset at about 56 h). In terms of the solubility of $Ag_5IO_6$ in different organic solvents, methanol>>THF>acetone>acetonitrile.

Example 5—Storage Stability

Even at 90° C., at 14 and 28 days, grain growth occurred (from 14 Å at Day 0, to 62 Å at Day 14, to 94 Å at Day 28) but no compositional change was observed (the material remained 100% $Ag_5IO_6$). Since stability at 54° C. for 28 days suggests a shelf life of >2 years at room temperature, this data demonstrates very good storage stability of $Ag_5IO_6$. The $Ag_5IO_6$ had a relatively high water content as-made (137370 ppm), indicating that even relatively "wet" product as dried using the current drying technique has very good storage stability. With DSC and TGA analysis, $Ag_5IO_6$ is stable past 400° C., indicating that it can be put through the thermal processing required to generate some medical devices without decomposition, although the grain size may increase.

Example 6—$Ag_5IO_6$ Photostability

The purpose of this study was to assess the photostability of $Ag_5IO_6$ in accordance with the FDA's 1997 recommendations regarding the photostability testing of new products. $Ag_5IO_6$ was ground, spread thinly on watch glasses, protected from foreign objects, and, along with aluminum foil covered controls, the watch glasses were placed face up under cool-light metal halide lamps such that the samples were receiving at least 700 fc, and the lux exposure was measured regularly until greater than 1.3 million lux hours exposure had occurred. The samples were then submitted for XRD. After greater than 1.3 million lux hours exposure, the material was still 100% $Ag_5IO_6$. $Ag_5IO_6$ has very good photostability and does not need to be stored protected from light.

Example 7

The purpose of this study was to evaluate the clarity, weight vs. time under potentially drying conditions, and dispensing properties of various hydrogels after the incorporation of $Ag_5IO_6$. $Ag_5IO_6$ is a black solid that is thought to be slightly soluble in water, stable at high temperatures and to have properties that allow for compatibility with metals, dressings, and gels.

For each sample preparation described below, the samples were mixed in a small glass container (e.g. beaker or flask). A small magnetic stir bar was placed in the glass container, which was sealed with parafilm and stirred on a magnetic stirrer. Once the sample appeared well-mixed, it was transferred to a scintillation vial. Samples were protected from light using aluminum foil. The $Ag_5IO_6$ did not dissolve in all of these gels, in which case, samples were taken from a well stirred dispersion. If the powder gels without $Ag_5IO_6$ were too thin for testing, the gels were re-made in a higher concentration to have a similar viscosity as the pre-made/ commercial gels. The amount of powder and water used was recorded.

AquaThik™: 3% AquaThik™ was made by combining 0.3 g AquaThik™ with 10 mL $ddH_2O$. 3% AquaThik™ with 500 ppm $Ag_5IO_6$ was made by combining 0.3 g AquaThik™ with 5 mg $Ag_5IO_6$ and then adding 10 mL $ddH_2O$. 3% AquaThik™ with 10000 ppm $Ag_5IO_6$ was made by combining 0.3 g AquaThik™ with 100 mg $Ag_5IO_6$ and then adding 10 mL $ddH_2O$.

SteriLub™: SteriLub™ with 500 ppm $Ag_5IO_6$ was made by combining 5 mg $Ag_5IO_6$ with 10 g SteriLub™. SteriLub™ with 10000 ppm $Ag_5IO_6$ was made by combining 100 mg $Ag_5IO_6$ with 10 g SteriLub™.

DuoDERM®: DuoDERM® with 500 ppm $Ag_5IO_6$ was made by adding 5 mg $Ag_5IO_6$ to 10 g DuoDERM®. DuoDERM® with 10000 ppm $Ag_5IO_6$ was made by adding 100 mg $Ag_5IO_6$ to 10 g DuoDERM®.

Carboxymethylcellulose (CMC): A 4% CMC gel was made by combining 0.4 g CMC with 10 mL $ddH_2O$. A 4% CMC gel with 500 ppm $Ag_5IO_6$ was made by combining 0.4 g CMC with 5 mg $Ag_5IO_6$, then adding 10 mL $ddH_2O$. A 4% CMC gel with 10000 ppm $Ag_5IO_6$ was made by combining 0.4 g CMC with 100 mg $Ag_5IO_6$, then adding 10 mL $ddH_2O$.

Lubrajel® PF: Lubrajel® PF with 500 ppm $Ag_5IO_6$ was made by adding 5 mg $Ag_5IO_6$ to 10 g Lubrajel® PF. Lubrajel® PF with 10000 ppm $Ag_5IO_6$ was made by adding 100 mg $Ag_5IO_6$ to 10 g Lubrajel® PF.

Lubrajel® RC: Lubrajel® RC with 500 ppm $Ag_5IO_6$ was made by adding 5 mg $Ag_5IO_6$ to 10 g Lubrajel® RC. Lubrajel® RC with 10000 ppm $Ag_5IO_6$ was made by adding 100 mg $Ag_5IO_6$ to 10 g Lubrajel® RC.

IntraSite Gel: IntraSite with 500 ppm $Ag_5IO_6$ was made by adding 5 mg $Ag_5IO_6$ to 10 g IntraSite. IntraSite with 10000 ppm $Ag_5IO_6$ was made by adding 100 mg $Ag_5IO_6$ to 10 g IntraSite.

SoloSite Gel: SoloSite with 500 ppm $Ag_5IO_6$ was made by adding 5 mg $Ag_5IO_6$ to 10 g SoloSite. SoloSite with 10000 ppm $Ag_5IO_6$ was made by adding 100 mg $Ag_5IO_6$ to 10 g SoloSite.

Gelrite: 0.4% Gelrite was made by adding 0.04 g Gelrite powder to 10 mL $ddH_2O$. 0.4% Gelrite with 500 ppm $Ag_5IO_6$ was made by combining 0.04 g gelrite powder with 5 mg $Ag_5IO_6$ and then adding it to 10 mL $ddH_2O$. 0.4% Gelrite with 10000 ppm $Ag_5IO_6$ was made by combining 0.04 g Gelrite powder with 100 mg $Ag_5IO_6$ and then adding it to 10 mL $ddH_2O$.

In most gels, addition of $Ag_5IO_6$ at increasing concentrations caused the gels to become an opaque brown. For two of the gels, opacity was not achieved due to particles of $Ag_5IO_6$ clumping in the gel rather than a uniform dispersion or dissolution of the $Ag_5IO_6$.

The dispensing behavior of the CMC, Lubrajel PF, Lubrajel RC, and Gelrite gels were affected by the addition of Ag$_5$IO$_6$ while the other gels tested were not. Based on the results of the dispensing behavior tests, the CMC gel increased in viscosity, and the Lubrajel RC, Lubrajel PF, and Gelrite gels decreased in viscosity after the addition of Ag$_5$IO$_6$, thus no clear overall pattern was observed, but in select gels, the viscosity was impacted.

For the majority of the gels, adding Ag$_5$IO$_6$ had no impact on the % weight loss over time due to water loss at a set temperature and humidity. In the CMC gel only, adding 10000 ppm Ag$_5$IO$_6$ reduced water loss.

Example 8

The gels of examples 1 and 7 were tested against additional species. Commercial gels (without Ag$_5$IO$_6$)—None of the commercial gels performed well against *P. aeruginosa, S. aureus, S. epidermidis* or *C. albicans*. Overall, the three commercial gels did not have a significant antimicrobial effect on the *P. aeruginosa*. The SilvaSorb, Siver-Sept, and Elta Silver gel did not have any antimicrobial effect on *S. aureus*. The Silver-Sept, SilvaSorb, and Elta Silvergel gels did not have any antimicrobial effect on *S. epidermidis*. All 3 commercial gels tested did not produce an antimicrobial effect against *C. albicans*.

Ag$_5$IO$_6$ Gels: Based on zone size and longevity, the 50000 ppm Aquathik, 50000 ppm Lubrajel RC, and 50000 ppm Lubrajel PF gels had the greatest overall longevity and zone size against *P. aeruginosa*. All three gels had zones of inhibition lasting 7 days. The 50000 ppm carboxymethylcellulose gel also performed well against *P. aeruginosa*, but only had zones of inhibition lasting 6 days. The 10000 ppm Ag$_5$IO$_6$ gels only had zones of inhibition lasting 3 days, which shows that the higher gel concentration is required to produce long lasting zones of inhibition.

For *S. aureus*, the 10000 ppm Ag$_5$IO$_6$ gels lasted a minimum of 2 days (Intrasite) and a maximum of 5 days (carboxymethylcellulose). There were four 50000 ppm gels that had zones lasting the entire 10 days. These included the Aquathik, Lubrajel RC, Lubrajel PF, and carboxymethylcellulose gels. These gels had good longevity and zone size against *S. aureus*.

For *S. epidermidis*, only the 50000 ppm carboxymethylcellulose gel had zones of inhibition lasting 10 days. All other gels had zones lasting 7 days or less. The 10000 ppm Ag$_5$IO$_6$ gels had zones of inhibition lasting between 2 and 3 days.

For *C. albicans*, all of the Ag$_5$IO$_6$ gels had zones of inhibition on Day 1, but on Day 2 a less dense lawn of bacteria grew within the visible zone. Based on this, the Ag$_5$IO$_6$ gels were deemed to not have produced any zones of inhibition on Day 2. The Ag$_5$IO$_6$ gels were more effective against *C. albicans* than the commercial gels in producing an antimicrobial effect, but did not achieve the desired longevity of about 10 days. Therefore, the Ag$_5$IO$_6$ gels were not effective against *C. albicans*.

We claim:

1. A method of treating a microbial contaminant comprising:
   contacting a substrate with one or more antimicrobial compounds that release an anion of 3$^-$ charge containing both silver and orthoperiodate, the antimicrobial compound selected from the group consisting of:
   pentasilver hexaoxoiodate (formula, Ag$_5$IO$_6$);
   Ag$_x$H$_y$IO$_6$, where x is a value between 1 and 5, and y is the corresponding value between 0 and 4 necessary to achieve the correct total positive charge of 5;
   Ag$_x$M$_y$IO$_6$, where x is a value between 1 and 5, y is a corresponding value between 0 and 4 necessary to achieve the correct total positive charge of 5, and M is one or more metals or hydrogen and any combinations thereof; and
   any combinations thereof, excluding compounds containing silver of a valency greater than 1, and
   contacting the microbial contaminant with the antimicrobial compound on the substrate.

2. The method of claim 1, wherein the microbial contaminant is a biofilm.

3. The method of claim 1, wherein the antimicrobial compound is in the form of a coating, powder, gel, spray, dipping solution, or lubricant.

4. The method of claim 1, wherein treating a microbial contaminant comprises increasing an antimicrobial characteristic of an article.

5. The method of claim 1, wherein treating a microbial contaminant comprises a method of reducing microbial contamination on a substrate.

6. The method of claim 5, wherein reducing microbial contamination on a substrate comprises forming the antimicrobial compound from a diperiodatoargentate, and contacting the substrate, thereby coating the substrate with the antimicrobial compound to prevent or reduce microbial contamination.

7. An article of manufacture, said article comprising one or more antimicrobial compounds that release an anion of 3$^-$ charge containing both silver and orthoperiodate, the antimicrobial compound selected from the group consisting of:
   pentasilver hexaoxoiodate (formula, Ag$_5$IO$_6$);
   Ag$_x$H$_y$IO$_6$, where x is a value between 1 and 5, and y is the corresponding value between 0 and 4 necessary to achieve the correct total positive charge of 5;
   Ag$_x$M$_y$IO$_6$, where x is a value between 1 and 5, y is a corresponding value between 0 and 4 necessary to achieve the correct total positive charge of 5, and M is one or more metals or hydrogen and any combinations thereof; and
   any combinations thereof, excluding compounds containing silver of a valency greater than 1; and
   wherein said article is coated by allowing the antimicrobial compound to form from a diperiodatoargentate while contacting the article or a portion thereof, thereby coating the article or a portion thereof with the antimicrobial compound to form an article having antimicrobial properties.

8. The method of claim 1, wherein the substrate comprises a catheter.

9. The method of claim 1, wherein the antimicrobial compound comprises a hydrogel.

10. The method of claim 1, wherein the substrate is selected from the group consisting of titanium, titanium containing alloys, titanium (grade 2), titanium (grade 5), aluminum, stainless steel, and polymer.

11. The article of claim 7, wherein the article comprises a catheter.

12. The article of claim 7, wherein the antimicrobial compound comprises a hydrogel.

13. The article of claim 7, wherein the article is selected from the group consisting of titanium, titanium containing alloys, titanium (grade 2), titanium (grade 5), aluminum, stainless steel, and polymer.

14. A medical device, comprising
   a substrate;
   one or more antimicrobial compounds that release an anion of 3$^-$ charge containing both silver and orthoperiodate, the one or more antimicrobial compounds being associated with the substrate, and the antimicrobial compound selected from the group consisting of:

pentasilver hexaoxoiodate (formula, $Ag_5IO_6$);

$Ag_xH_yIO_6$, where x is a value between 1 and 5, and y is the corresponding value between 0 and 4 necessary to achieve the correct total positive charge of 5;

$Ag_xM_yIO_6$, where x is a value between 1 and 5, y is a corresponding value between 0 and 4 necessary to achieve the correct total positive charge of 5, and M is one or more metals or hydrogen and any combinations thereof; and any combinations thereof, excluding compounds containing silver of a valency greater than 1.

15. The medical device of claim 14, wherein the medical device comprises a catheter.

16. The medical device of claim 15, further including a coating on a surface of the substrate of the catheter, wherein the coating comprises the one or more antimicrobial compounds.

17. The medical device of claim 14, wherein the substrate comprises a polymer and the one or more antimicrobial compounds are incorporated in the polymer.

18. The medical device of claim 14, wherein the medical device includes a coating on a surface of the substrate, wherein the coating comprising the one or more antimicrobial compounds.

19. The medical device of claim 18, wherein the coating comprising a polymer and the one or more antimicrobial compounds.

20. The medical device of claim 14, wherein the antimicrobial compound comprises a hydrogel.

* * * * *

UNITED STATES PATENT AND TRADEMARK OFFICE
CERTIFICATE OF CORRECTION

PATENT NO. : 11,116,865 B2
APPLICATION NO. : 16/548062
DATED : September 14, 2021
INVENTOR(S) : Merle E. Olson, Patricia L. Nadworny and Graeme Prosperi-Porta It is certified that error appears in the above-identified patent and that said Letters Patent is hereby corrected as shown below:

In the Claims

In Column 16, Line 25, Claim 6, delete "prevent or" therefor.

Signed and Sealed this
Ninth Day of April, 2024

Katherine Kelly Vidal
*Director of the United States Patent and Trademark Office*